United States Patent

Okumura (10) Patent No.: US 11,642,425 B2
(45) Date of Patent: May 9, 2023

(54) METHOD FOR INACTIVATING BACTERIA OR VIRUSES AND INACTIVATING APPARATUS FOR BACTERIA OR VIRUSES

(71) Applicant: Ushio Denki Kabushiki Kaisha, Tokyo (JP)

(72) Inventor: Yoshihiko Okumura, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 17/393,511

(22) Filed: Aug. 4, 2021

(65) Prior Publication Data

US 2022/0040344 A1 Feb. 10, 2022

(30) Foreign Application Priority Data

Aug. 5, 2020 (JP) .............................. JP2020-133323

(51) Int. Cl.
*A61L 2/10* (2006.01)
*A61L 2/24* (2006.01)
(Continued)

(52) U.S. Cl.
CPC .................. *A61L 2/10* (2013.01); *A61L 2/24* (2013.01); *A61L 2/26* (2013.01); *A61L 2202/11* (2013.01); *A61L 2202/14* (2013.01); *F24F 8/22* (2021.01)

(58) Field of Classification Search
CPC ..... A61L 2/10; A61L 2/24; A61L 2/26; A61L 2/28; A61L 2202/11; A61L 2202/14; A61L 2202/25
See application file for complete search history.

(56) References Cited

U.S. PATENT DOCUMENTS

2018/0132508 A1 5/2018 Matsui
2019/0038914 A1 2/2019 Igarashi et al.
(Continued)

FOREIGN PATENT DOCUMENTS

CN  108601854 A  9/2018
CN  111050846 A  4/2020
(Continued)

OTHER PUBLICATIONS

The European search report (under R. 61 or R. 63 EPC) or the supplementary european search report (Art. 153(7) EPC) issued by the European Patent Office dated Dec. 6, 2021, which corresponds to European Patent Application No. 21189068.6-1104 and is related to U.S. Appl. No. 17/393,511.
(Continued)

*Primary Examiner* — Timothy C Cleveland
(74) *Attorney, Agent, or Firm* — Studebaker & Brackett PC (57) ABSTRACT

Provided are a method and an apparatus for inactivating bacteria or viruses attached to an object while suppressing generation of a strange odor. The method for inactivating bacteria or viruses includes a step (a) of irradiating with ultraviolet light having an optical output at a specific wavelength in a range of 200 nm to 235 nm. The step (a) is a step of irradiating with the ultraviolet light is performed so that an irradiance (X) [mW/cm²] (X>0) and an integrated irradiation dose within two hours (Y) [mJ/cm²] satisfy the following formula (1)

$$0 < Y < 10.704 X^{-0.373} \qquad (1).$$

9 Claims, 8 Drawing Sheets

(51) Int. Cl.
   *A61L 2/26* (2006.01)
   *F24F 8/22* (2021.01)

(56) References Cited

U.S. PATENT DOCUMENTS

| | | | |
|---|---|---|---|
| 2020/0101183 | A1 | 4/2020 | Dijkstra et al. |
| 2020/0234941 | A1 | 7/2020 | Yagyu et al. |
| 2020/0237940 | A1 | 7/2020 | Van et al. |
| 2020/0246632 | A1 | 8/2020 | Naito |
| 2021/0015959 | A1 | 1/2021 | Goseki et al. |
| 2021/0379215 | A1* | 12/2021 | Kelleher ............... A61L 2/0047 |

FOREIGN PATENT DOCUMENTS

| | | | |
|---|---|---|---|
| EP | 3 421 053 | A1 | 1/2019 |
| JP | 6025756 | B2 | 11/2016 |
| JP | 2018-517488 | A | 7/2018 |
| JP | 2018-130535 | A | 8/2018 |
| JP | 2019-103816 | A | 6/2019 |
| WO | 00/28552 | A1 | 5/2000 |
| WO | 2012/122210 | A1 | 9/2012 |
| WO | 2016/196904 | A1 | 12/2016 |
| WO | 2017/221285 | A1 | 12/2017 |
| WO | 2018/131582 | A1 | 7/2018 |
| WO | 2019/065126 | A1 | 4/2019 |
| WO | 2019/164810 | A1 | 8/2019 |
| WO | 2019/186880 | A1 | 10/2019 |
| WO | 2019/190967 | A1 | 10/2019 |
| WO | 2020/203754 | A1 | 10/2020 |

OTHER PUBLICATIONS

An Office Action; "Notice of Reasons for Refusal", mailed by the Japanese Patent Office dated Aug. 17, 2021, which corresponds to Japanese Patent Application No. 2020-195386 and is related to U.S. Appl. No. 17/393,511; with English language translation.

Manuela Buonanno et.al., "207-nm UV Light—A Promising Tool for Safe Low-Cost Reduction of Surgical Site Infections. I: In Vitro Studies", Plos One, vol. 8, pp. 1-7, Oct. 15, 2013.

Ueno Hiroyuki et al., Rough Indication of Odor Index, The Tokyo Metropolitan Research Institute for Environmental Protection, "Annual report of the Tokyo Metropolitan Research Institute for Environmental Protection 2008", pp. 47-51, 2008.

"Decision to Grant" Office Action issued in JP 2020-133323; mailed by the Japanese Patent Office dated Aug. 20, 2021.

Communication pursuant to Article 94(3) EPC issued by the European Patent Office dated Jul. 25, 2022, which corresponds to European Patent Application No. 21 189 068.6-1101 and is related to U.S. Appl. No. 17/393,511.

An Office Action mailed by China National Intellectual Property Administration dated Jan. 24, 2022, which corresponds to Chinese Patent Application No. 202110549053.9 and is related to U.S. Appl. No. 17/393,511; with English language translation.

Decision of Final Rejection mailed by China National Intellectual Property Administration dated Jun. 2, 2022, which corresponds to Chinese Patent Application No. 202110549053.9 and is related to U.S. Appl. No. 17/393,511; with English language translation.

Communication pursuant to Article 94(3) EPC issued by the European Patent Office dated Feb. 10, 2023, which corresponds to European Patent Application No. 21189068.6-1101 and is related to U.S. Appl. No. 17/393,511.

* cited by examiner

METHOD FOR INACTIVATING BACTERIA OR VIRUSES AND INACTIVATING APPARATUS FOR BACTERIA OR VIRUSES

BACKGROUND OF THE INVENTION

Field of the Invention

The present invention relates to a method for inactivating bacteria or viruses, and particularly relates to a method for inactivating bacteria or viruses using ultraviolet light. The present invention also relates to an inactivating apparatus for bacteria or viruses.

Description of the Related Art

A conventional technique for sterilization by irradiating ultraviolet light is known. DNA shows the highest absorption characteristics at wavelengths around 260 nm. A low-pressure mercury lamp has a strong emission spectrum around a wavelength of 254 nm. Accordingly, a technique of using a low-pressure mercury lamp for sterilization is widely availed.

However, exposure of a human body to ultraviolet light in such a wavelength range is known to cause a risk of affecting the human body. The skin is divided into three parts from superficial to deep: the epidermis, the dermis, and the hypodermis deeper than the dermis, and the epidermis is further divided into four layers from superficial to deep: the stratum corneum, the stratum granulosum, the stratum spinosum, and the stratum germinativum. When a human body is exposed to ultraviolet light with a wavelength of 254 nm, the ultraviolet light penetrates the stratum corneum, reaches the stratum granulosum and the stratum spinosum, and in some cases the stratum germinativum, and is absorbed by DNA of the cells within these layers. This results in the risk of skin cancer.

From such a viewpoint, Patent Document 1 below discloses a technique for sterilization in a medical setting using ultraviolet light with a wavelength in the range of 200 nm to 235 nm, while avoiding risks to the human body.

PATENT DOCUMENT

Patent Document 1: JP 6025756 B2

NON-PATENT DOCUMENTS

Non-Patent Document 1: Wakio Torinuki et al. "Emission spectral analysis of ultraweak chemiluminescence of UVB-irradiated linolenic acid and squalene peroxides", The Japanese journal of dermatology, Vol. 92, No. 1, 1982

Non-Patent Document 2: Manuela Buonanno et. al., "207-nm UV Light—A Promising Tool for Safe Low-Cost Reduction of Surgical Site Infections. I: In Vitro Studies", Plos One, 2013

Non-Patent Document 3: The Tokyo Metropolitan Research Institute for Environmental Protection, "Annual report of the Tokyo Metropolitan Research Institute for Environmental Protection 2008", 2008

SUMMARY OF THE INVENTION

Through intensive studies, the present inventor has newly discovered a problem in which a strange odor is generated when ultraviolet light is irradiated to the surface of an object (e.g., a table, a desk, a wall) in a room to inactivate bacteria or viruses present on the surface, using an ultraviolet light source that has an optical output at a wavelength in the range of 200 nm to 235 nm. The present inventor presumes that this problem is caused by the following reason.

The object such as a table, a desk, or a wall in a room is likely to be touched by human hands. When the object is touched by human hands, the surface of the object is attached with human sebum (e.g., triglycerides, squalene, wax esters, etc.) and free fatty acids (palmitoleic acid) decomposed from the sebum.

Squalene, a kind of sebum, produces squalene monohydroperoxide (SQHPO) when ultraviolet light is irradiated. Here, when SQHPO and palmitoleic acid coexist, strange odorous components (odor sources) such as nonenal, hexanal, octenal, and heptanal are produced. This is similar to the principle of the generation of aging odor in the human body, which usually progresses slowly due to temperature of living environment and ultraviolet light contained in sunlight, causing the skin to produce a strange odor.

However, it is considered that the above reaction was significantly accelerated when the surface of the object was irradiated with ultraviolet light with a wavelength of 200 nm to 235 nm, resulting in the generation of a strange odor at a level detectable by humans.

In light of such a problem, it is an object of the present invention to provide a method and an apparatus for inactivating bacteria or viruses attached to an object while suppressing generation of a strange odor.

The present invention is directed to a method for inactivating bacteria or viruses, the method including a step (a) of irradiating with ultraviolet light having an optical output at a specific wavelength in a range of 200 nm to 235 nm, wherein the step (a) is a step of irradiating with the ultraviolet light so that an irradiance (X) [mW/cm$^2$] (X>0) and an integrated irradiation dose within two hours (Y) [mJ/cm$^2$] satisfy the following formula (1).

$$0 < Y < 10.704 X^{-0.373} \tag{1}$$

Irradiating ultraviolet light in such a way as to satisfy the above formula (1) enables to inactivate bacteria or viruses while suppressing the generation of a strange odor. This will be described later in the section "DETAILED DESCRIPTION OF PREFERRED EMBODIMENTS". Note that irradiating the ultraviolet light in such a way that $Y < 8.563 X^{-0.373}$ enhances the effect of suppressing the generation of a strong odor.

The step (a) may be a step of irradiating with the ultraviolet light so that the irradiance (X) [mW/cm$^2$] (X>0) and the integrated irradiation dose within two hours (Y) [mJ/cm$^2$] satisfy the following formula (2).

$$0 < Y < 0.4534 X^{-0.697} \tag{2}$$

Irradiating ultraviolet light in such a way as to satisfy the above formula (2) enables to inactivate bacteria or viruses while suppressing the generation of a strange odor more significantly. This will be described later in the section "DETAILED DESCRIPTION OF PREFERRED EMBODIMENTS". Note that irradiating the ultraviolet light in such a way that $Y < 0.36272 X^{-0.697}$ enhances the effect of suppressing the generation of a strong odor.

The step (a) may be a step of irradiating with the ultraviolet light at the irradiance (X) [mW/cm$^2$] (X≥0.0002).

The step (a) may be a step of irradiating with the ultraviolet light at the irradiance (X) [mW/cm$^2$] (X≥0.001).

The step (a) may be a step of intermittently irradiating with the ultraviolet light so that the formula (1) is satisfied.

The description "intermittently irradiating" as used herein refers, for example, to the repeated process of continuously irradiating for a predetermined first time and then stopping the irradiation for a predetermined second time. In this process, the time of continuous irradiation (the first time above) and the irradiation interval (the second time above) may be changed in each case.

In the method for inactivating bacteria or viruses, the step (a) may be a step of irradiating with the ultraviolet light indoors, and the method may further include a step (b) of exchanging indoor air one or more times within two hours.

The present invention is also directed to an inactivating apparatus for bacteria or viruses, the apparatus including:

a light source that emits ultraviolet light having an optical output at a specific wavelength in a range of 200 nm to 235 nm; and a controller that controls an emission intensity of the light source, wherein the controller controls the emission intensity of the light source so that an irradiance (X) [mW/cm$^2$] (X>0) on an irradiated surface and an integrated irradiation dose within two hours (Y) [mJ/cm$^2$] satisfy the following formula (1).

$$0 < Y < 10.704X^{-0.373} \quad (1)$$

In the apparatus, the controller may control the emission intensity of the light source so that the irradiance (X) [mW/cm$^2$] (X>0) on the irradiated surface and the integrated irradiation dose within two hours (Y) [mJ/cm$^2$] satisfy the following formula (2).

$$0 < Y < 0.4534X^{-0.697} \quad (2)$$

The inactivating apparatus for bacteria or viruses may further include an irradiance meter that measures the irradiance (X) on the irradiated surface and sends the measured irradiance (X) to the controller.

In the apparatus, the controller may control the light source so that the light source is intermittently turned on while the formula (1) is satisfied.

According to the present invention, it is possible to inactivate bacteria or viruses attached to an object while suppressing generation of a strange odor.

DETAILED DESCRIPTION OF THE PREFERRED EMBODIMENTS

Embodiments of a method for inactivating bacteria or viruses and an inactivating apparatus according to the present invention will be described with reference to the drawings.

In this specification, "inactivation" is a concept that encompasses killing bacteria or viruses, or causing them to lose their infectivity or toxicity. Further, herein, "bacteria" refers to microorganisms including fungi (molds).

Figure 1:
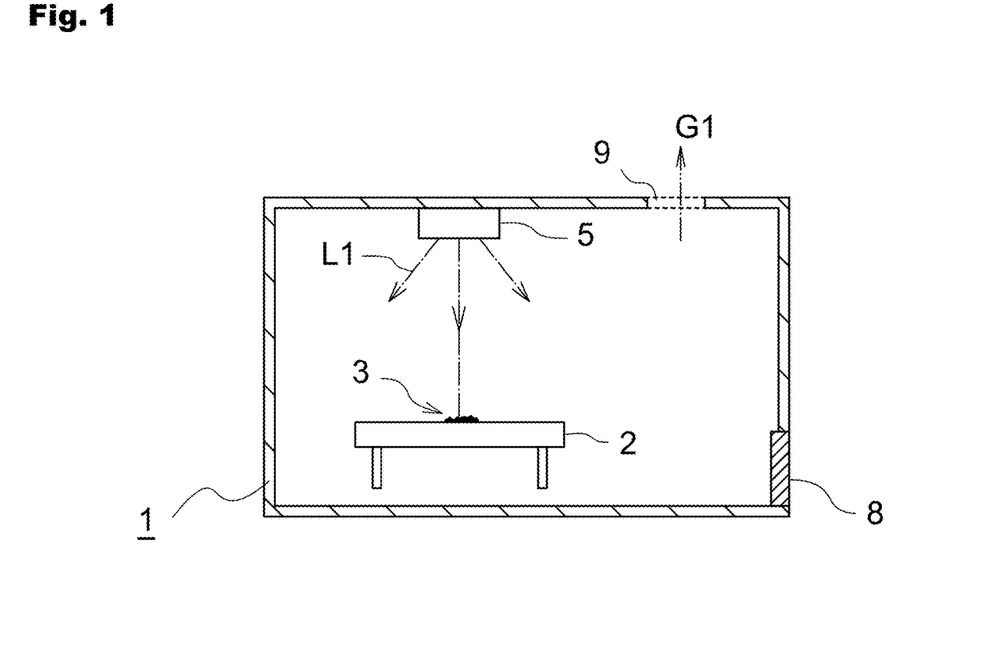
FIG. 1 is a diagram schematically showing a state in which a method for inactivating bacteria or viruses according to the present invention is carried out.

FIG. 1 is a diagram schematically showing a state in which the method for inactivating bacteria or viruses according to the present invention is carried out. The method of the present invention relates to a method for inactivating bacteria or viruses (hereinafter referred to as "germs 3") by irradiating ultraviolet light L1 emitted from an inactivating apparatus 5 onto a processing target 2 that is assumed to have the germs 3 attached to its surface. The term "germs" is a concept that encompasses "bacteria" and "viruses". In other words, germs 3 are bacteria and/or viruses.

In this embodiment, the processing target 2 is placed in a room 1. The room 1 is configured to allow ventilation of the air inside the room 1 through a door 8, an air vent 9, gaps, and the like. However, as will be described later, the method according to the present invention can be implemented not only in the case where the processing target 2 is placed in the room 1, but also in the case where the processing target 2 is placed "in a building" including a corridor or the like.

In Japan, the ventilation frequency of the room 1 in a building is required to be 0.5 times/hour or more by the Building Standards Law, and therefore, the air in the room 1 is supposed to be changed at least once every two hours. In other countries such as Norway, Sweden, Finland, Denmark, Belgium, France, Germany, Swiss, and Canada, it is mandatory or recommended that the ventilation frequency be at least 0.5 times/hour. In other words, the air in the room 1 is assumed to be changed at least once every two hours.

This means that even if a strange odor is generated in the room 1, the odor will be removed by ventilation as time passes. In other words, when a cause of a strange odor exists in the room 1, it is important to suppress the generation of the odor per some period of time (2 hours) during which the odor is accumulated.

Note that the above standard is established on the assumption that the building is highly airtight, and therefore conditions for suppressing generation of a strange odor are strict. For example, in the case of wooden buildings having low airtightness and large rooms or spaces having a height of three meters or more, smell is less likely to be accumulated, and therefore it is easy to reduce generation of a strange odor.

The inactivating apparatus 5 includes a light source that emits ultraviolet light L1. The ultraviolet light L1 has an optical output at a specific wavelength in the range of 200 nm to 235 nm. The ultraviolet light L1 may be one having a main peak wavelength in the range of 200 nm to 235 nm. Alternatively, the ultraviolet light L1 may be one having a main peak wavelength outside the range of 200 nm to 235 nm but having an optical output in a wavelength band that is at least part of the range from 200 nm to 235 nm.

Figure 2:
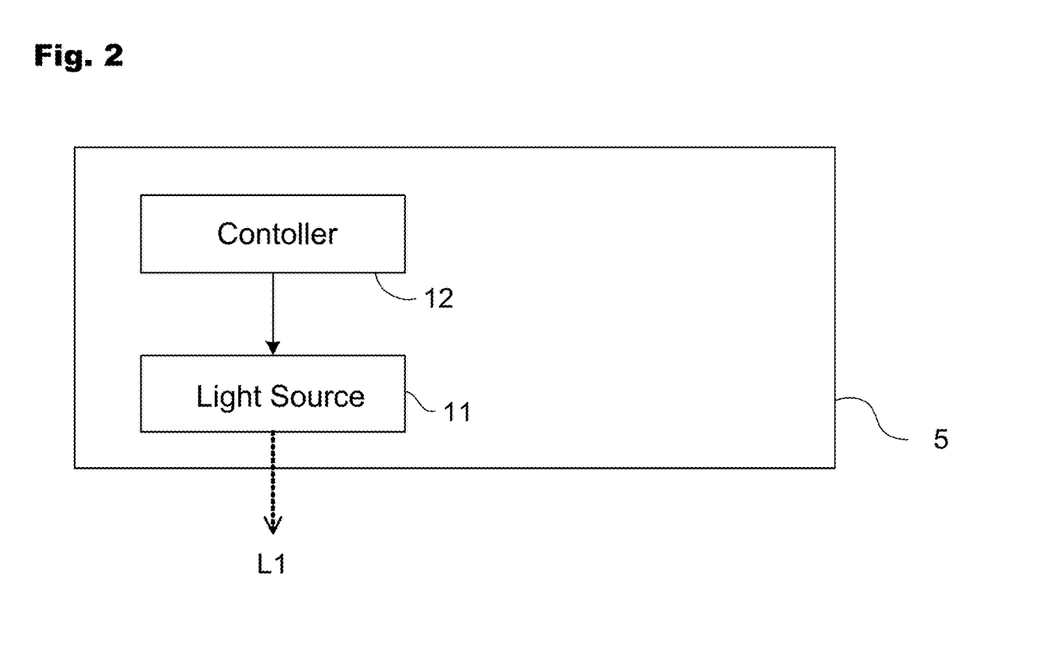
FIG. 2 is a block diagram schematically showing a structure of an inactivating apparatus.

FIG. 2 is a block diagram schematically showing the structure of the inactivating apparatus 5. The inactivating apparatus 5 includes a light source 11 and a controller 12 that controls emission of light from the light source 11.

Figure 3:
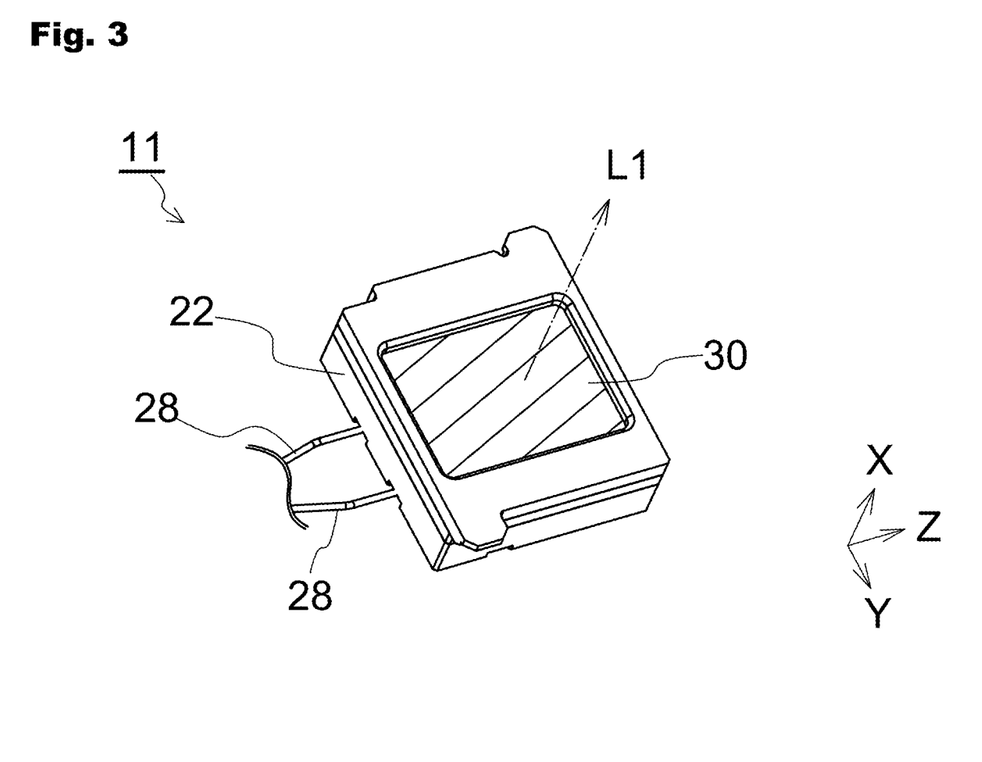
FIG. 3 is a perspective view schematically showing an example of the appearance of a light source.
Figure 4:
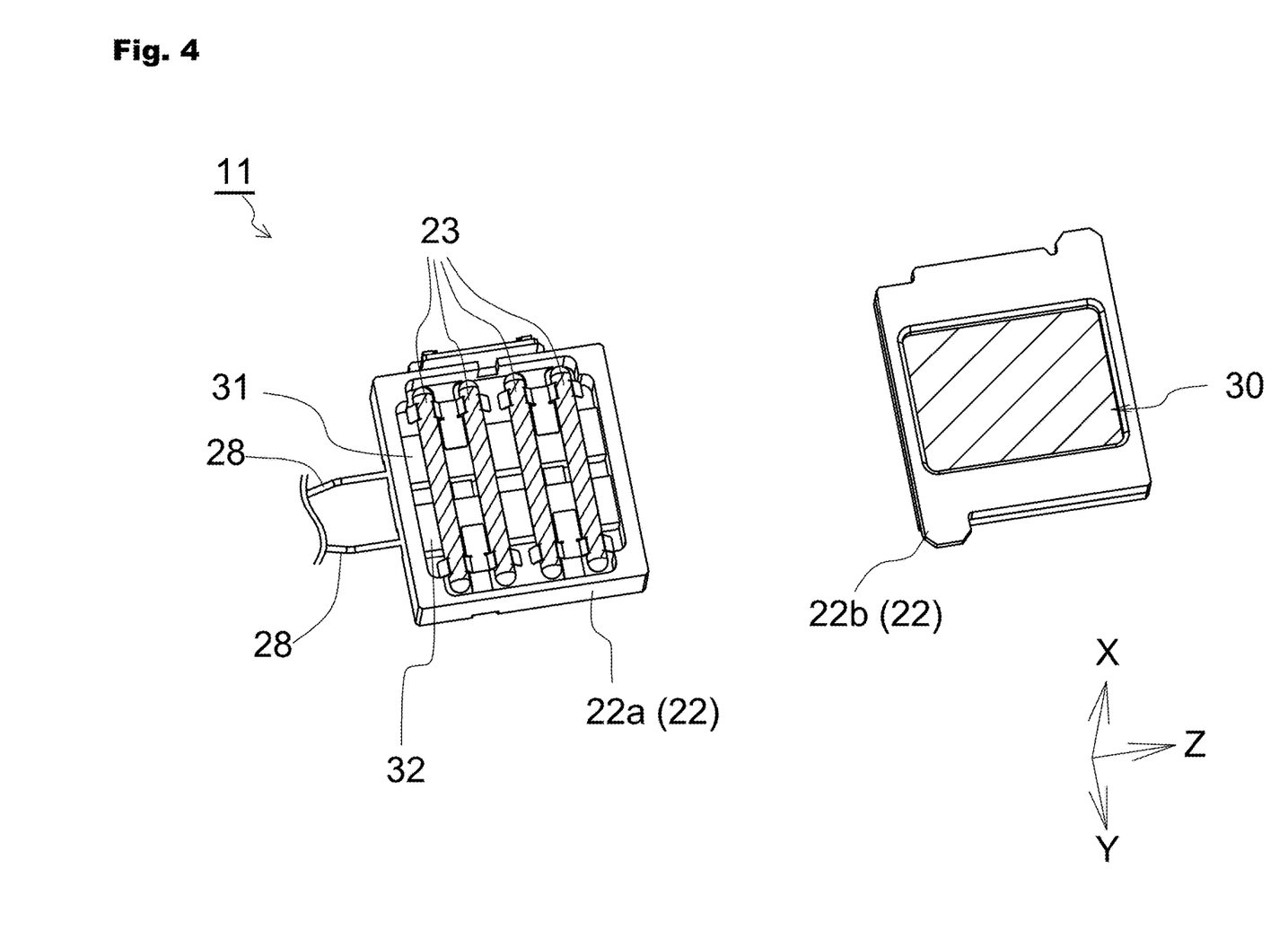
FIG. 4 is an exploded perspective view of the light source shown in FIG. 3.

FIG. 3 is a perspective view schematically showing an example of the appearance of the light source 11. FIG. 4 is a perspective view of the light source 11 shown in FIG. 3, in which a lamp house 22 is broken down into a main body casing 22a and a lid 22b.

The following description with reference to FIG. 3 to FIG. 5 will be made using an X-Y-Z coordinate system, where the extraction direction of the ultraviolet light L1 is an X direction and the plane orthogonal to the X direction is a YZ plane. More specifically, a direction parallel to the tube axis of an excimer lamp 23 is defined as a Y direction, and the direction orthogonal to the X direction and the Y direction is defined as a Z direction, as will be described later with reference to FIGS. 4 and 5.

As shown in FIG. 3 and FIG. 4, the light source 11 includes a lamp house 22 having a light extraction face 30 formed in one of the surfaces thereof. The lamp house 22 includes a main body casing 22a and a lid 22b, and the main body casing 22a houses excimer lamps 23 and electrode blocks (31, 32) therein. FIG. 4 shows a case where four excimer lamps 23 are housed in the lamp house 22 by way of example. The electrode blocks (31, 32) are electrically connected to power feeders 28 and constitute electrodes for feeding power to each of the excimer lamps 23. FIG. 5 is a plan view schematically showing a positional relationship between the excimer lamps 23 and the electrode blocks (31, 32).

Figure 5:
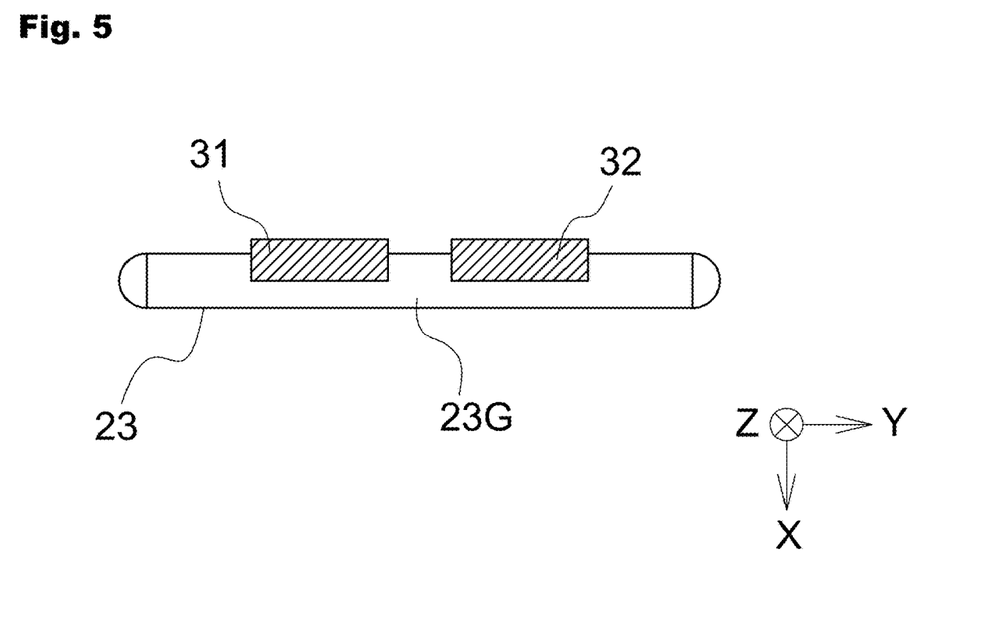
FIG. 5 is a plan view schematically showing a positional relationship between excimer lamps and electrode blocks in the light source shown in FIG. 3.

As shown in FIG. 3 to FIG. 5, the light source 11 in this embodiment has two electrode blocks (31, 32) arranged to contact the outer surface of the light-emitting tube of the respective excimer lamps 23. The electrode blocks (31, 32) are located at a distance in the Y direction. The electrode blocks (31, 32) are made of an electrical conductive material, preferably a material exhibiting reflectivity to ultraviolet light emitted from the excimer lamps 23. For example, the electrode blocks (31, 32) are both made of Al, an Al alloy, or stainless steel. Both the electrode blocks (31, 32) are arranged to span across each excimer lamp 23 with respect to the Z direction, while contacting the outer surface of the light-emitting tube of each excimer lamp 23.

The excimer lamps 23 each have a light-emitting tube with the Y direction as the tube axis direction, and the outer surface of the light-emitting tube of each of the excimer lamps 23 is in contact with the electrode blocks (31, 32) in positions separated from each other in the Y direction. A light-emitting gas 23G is enclosed within the light-emitting tubes of the excimer lamps 23. When a high-frequency AC voltage of, for example, about several kHz to 5 MHz is applied between the electrode blocks (31, 32) through the power feeders 28 (see FIG. 3) under control of the controller 12 (see FIG. 2), the voltage is applied to the light-emitting gas 23G through the light-emitting tubes of the excimer lamps 23. At this time, discharge plasma is generated in a discharge space filled with the light-emitting gas 23G, and atoms of the light-emitting gas 23G are excited to an excimer state. When the atoms shift to a ground state, excimer emission is generated.

The light-emitting gas 23G is made of a material that emits ultraviolet light L1 having an optical output at a specific wavelength in the range of 200 nm or more and 235 nm or less during emission of excimer light. For example, the light-emitting gas 23G contains KrCl or KrBr.

Figure 6:
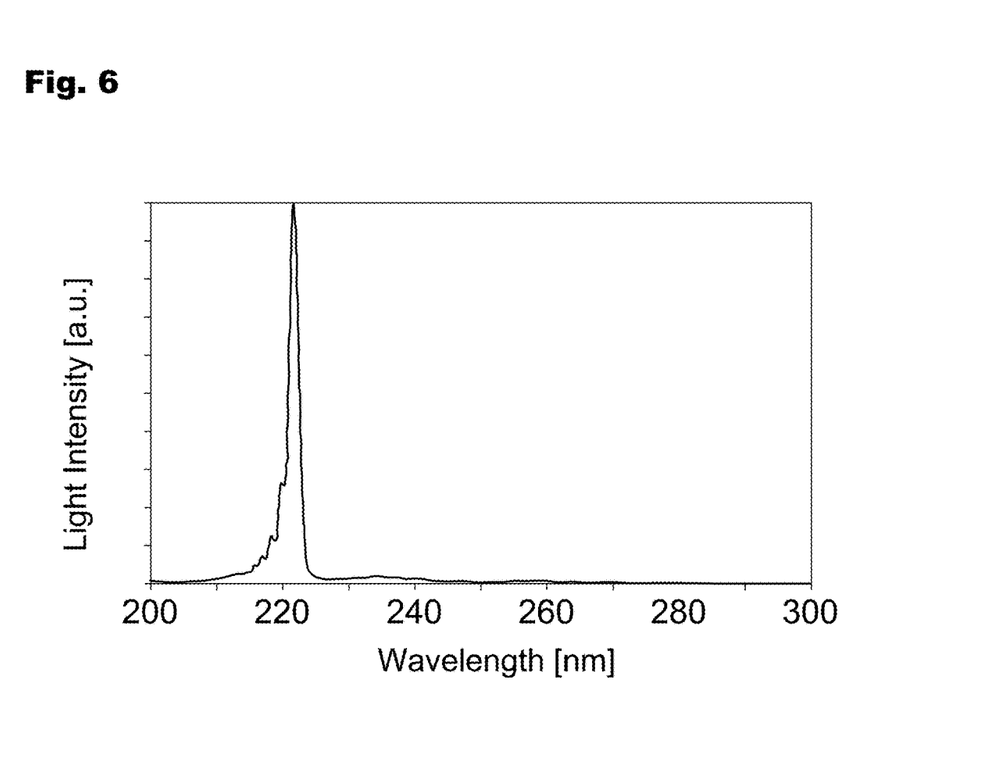
FIG. 6 is a graph showing the spectrum of ultraviolet light emitted from an excimer lamp using a light-emitting gas containing KrCl.

For example, when the light-emitting gas 23G contains KrCl, ultraviolet light L1 having a main peak wavelength of about 222 nm is emitted from the excimer lamps 23. When the light-emitting gas 23G contains KrBr, ultraviolet light L1 having a main peak wavelength of about 207 nm is emitted from the excimer lamps 23. FIG. 6 is a diagram showing the spectrum of ultraviolet light L1 emitted from the excimer lamps 23 using the light-emitting gas 23G containing KrCl.

When the inactivating method according to the present invention is carried out, the ultraviolet light L1 is emitted from the inactivating apparatus 5 (more specifically, from the light source 11) so that an irradiance (X) [mW/cm$^2$] (X>0) on the surface of the processing target 2 and an integrated irradiation dose within two hours (Y) [mJ/cm$^2$] satisfy the following formula (1) (step (a)).

$$0<Y<10.704X^{-0.373} \quad (1)$$

By irradiating with the ultraviolet light L1 in such a way as to satisfy this relational formula, it is possible to inactivate the germs 3 while suppressing generation of an odor in the room 1. This will be described below.

Figure 7A:
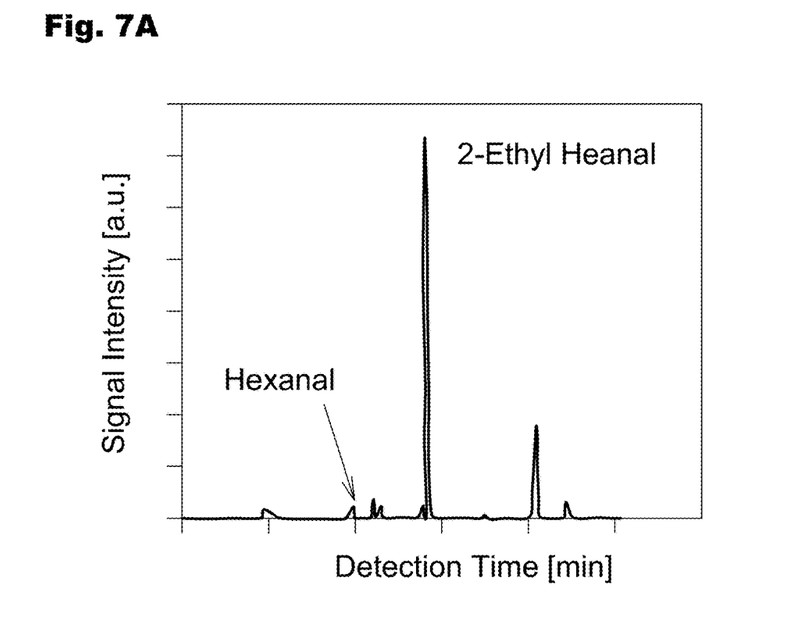
FIG. 7A is a graph showing the result of GC-MS analysis of air in a room performed after irradiation with ultraviolet light is performed in the room until a strange odor is generated.

FIG. 7A is a graph showing the result of GC-MS analysis on the air in the room 1 after detecting a strange odor by continuously irradiating the processing target 2 in the room 1 with the ultraviolet light L1 using a light source of the same type as the above-described light source 11. In FIG. 7A, the horizontal axis represents detection time, and the vertical axis represents detected intensity. According to FIG. 7A, it is confirmed that hexanal and 2-ethylhexanal are detected as odorous components in the air in the room 1 after ultraviolet light irradiation.

Figure 7B:
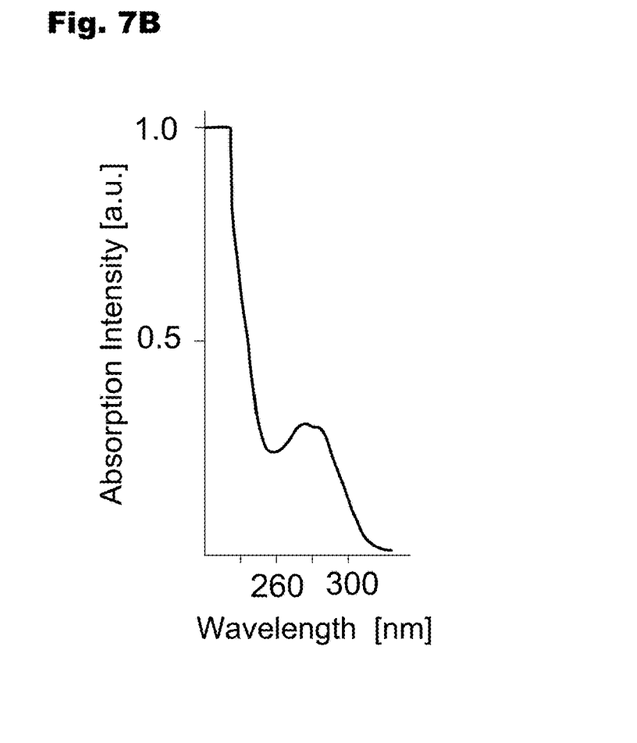
FIG. 7B is a graph showing the absorption spectrum of squalene.

FIG. 7B is a graph showing the absorption spectrum of a squalene solution having a molar concentration of 30 mol/L using ethanol as a solvent (see Non-Patent Document 1). As can be seen from FIG. 7B, squalene shows a significantly high absorbance for the ultraviolet light L1 with a wavelength of 200 to 235 nm. Note that this suggests that the problem of a strange odor is more likely to occur than when the germs 3 are inactivated by irradiation with ultraviolet light emitted from a low-pressure mercury lamp having a peak wavelength of 254 nm.

Figure 7C:
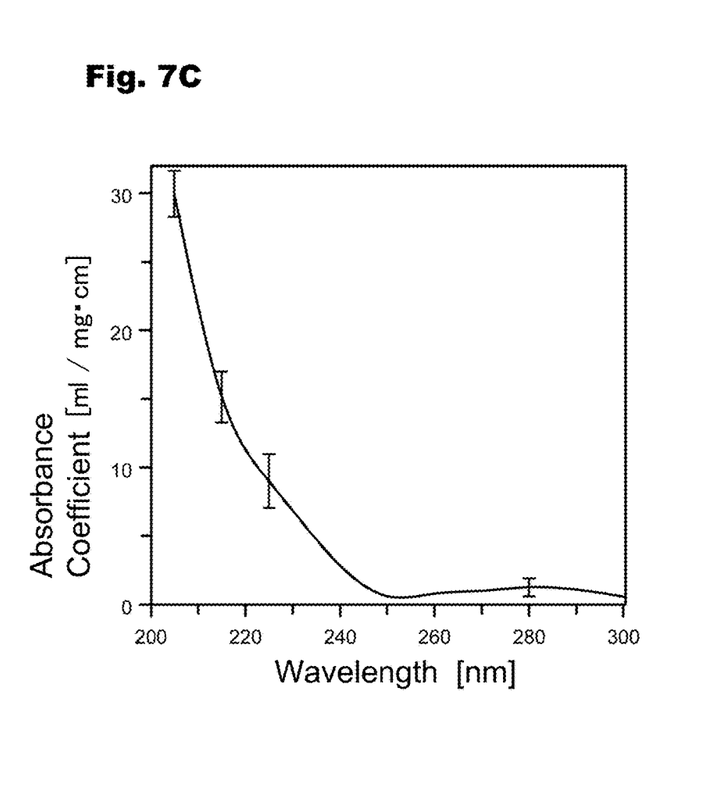
FIG. 7C is a graph showing a relationship between the absorbance coefficient of protein and wavelength.

FIG. 7C is a graph showing a relationship between the absorbance coefficient of protein and wavelength (see Non-Patent Document 2). As can be seen from FIG. 7C, the absorbance coefficient of protein remarkably increases as the wavelength shortens in a wavelength band shorter than 240 nm. Therefore, protein easily absorbs ultraviolet light with a wavelength of 200 nm to 235 nm, and this is presumed to cause the generation of a strange odor.

Based on the results shown in FIG. 7A, the present inventor has surmised that sebum attached to the surface of the processing target 2 is the cause of the strange odor generated when the germs 3 are inactivated by the ultraviolet light L1 having an optical output at a wavelength in the range of 200 nm to 235 nm. More specifically, the present inventor has surmised that when squalene, a kind of sebum, and a free fatty acid (palmitoleic acid) decomposed and generated from sebum are present on the surface of the processing target 2, squalene monohydroperoxide (SQHPO), which was generated by irradiating squalene with ultraviolet light L1 having an optical output at a wavelength in the range of 200 nm to 235 nm, reacted with palmitoleic acid to cause the production of odorous components such as hexanal.

[Examination 1]

An odor sensory test was performed using squalene (manufactured by FUJIFILM Wako Pure Chemical Corporation) and ethyl palmitoleate (manufactured by TOKYO OHKA KOGYO CO., LTD.) by changing irradiance and integrated irradiation dose. Hereinbelow, a test method will be described.

A plurality of sample bottles was prepared by mixing 1 μL of squalene and 0.1 μL of ethyl palmitoleate in a soda-lime glass bottle with dimensions of Φ41 mm (length)×Φ83.5 mm (width)×Φ152 mm (height), and UV light L1 was irradiated from the opening side of the wide-mouth bottle while maintaining a tight seal. The irradiance at the reagent area was derived from a previously-determined relationship between distance and irradiance.

The sample bottles hermetically sealed were irradiated with ultraviolet light L1 at four levels of irradiance of 0.003 mW/cm$^2$, 0.01 mW/cm$^2$, 0.1 mW/cm$^2$, and 1 mW/cm$^2$, respectively. The integrated irradiation dose was varied by changing the time of irradiation with ultraviolet light L1 at each irradiance level.

After the completion of ultraviolet light L1 irradiation treatment, the lid of each of the sample bottles was then opened and the air inside the sample bottle was sealed into a bag (hereinafter referred to as a "sample bag"). An odor sensory test of the air in the sample bag was conducted by five evaluators (M1 to M5). The details of the measurement method of the sensory test are as follows.

First, the evaluators sniffed the air in the sample bag. Then, the air in the sample bag was diluted 10-fold and the evaluators sniffed the diluted air. The dilution and the sensory test were repeated in the same way until the evaluators no longer sense any odor, and an odor index was calculated based on a dilution factor at which the evaluators no longer sensed any odor. The odor index N was calculated by the following formula (3) on the basis of an odor concentration D.

$$N = 10 \times \mathrm{Log}(D) \quad (3)$$

Note that in the above formula (3), the odor concentration D is a value indicating that no odor was sensed for the first time when D-fold dilution was performed. More specifically, in a case where the evaluator M1 still senses an odor even when the air in the sample bag is diluted 10-fold but does not sense any odor when the air in the sample bag is diluted 100-fold, the odor concentration D is 100. An odor is sensed when olfactory cells are stimulated by an odorant, and is more strongly sensed as the concentration of an odorant in the air increases. The strength of an odor is generally called odor intensity, and it is recognized that the Weber-Fechner law can be applied to represent a relationship between odor intensity and the concentration (amount) of an odorant. That is, there is a logarithmic relationship between odor intensity and odor concentration. Due to such circumstances, the method for evaluating the strength of an odor on the basis of the odor index N calculated by the above formula (3) is generally used.

Tables 1 to 4 show evaluation results obtained at irradiance levels X=0.003 mW/cm$^2$, 0.01 mW/cm$^2$, 0.1 mW/cm$^2$, and 1 mW/cm$^2$, respectively.

TABLE 1

| | | Irradiance (mW/cm$^2$) 0.003 Integrated Irradiation Dose (mJ/cm$^2$) | | | | |
|---|---|---|---|---|---|---|
| | | 1.0 | 10.0 | 30.0 | 50.0 | 100.0 |
| Evaluator | M1 | 10 | 10 | 20 | 20 | 30 |
| | M2 | 10 | 10 | 20 | 20 | 40 |
| | M3 | 10 | 10 | 10 | 20 | 20 |
| | M4 | 10 | 10 | 20 | 20 | 30 |
| | M5 | 10 | 10 | 10 | 20 | 20 |

TABLE 2

| | | Illuminance (mW/cm$^2$) 0.01 Integrated Irradiation Dose (mJ/cm$^2$) | | | | |
|---|---|---|---|---|---|---|
| | | 1.0 | 5.0 | 10.0 | 30.0 | 50.0 |
| Evaluator | M1 | 10 | 10 | 20 | 20 | 30 |
| | M2 | 10 | 20 | 20 | 30 | 40 |
| | M3 | 10 | 10 | 20 | 20 | 30 |
| | M4 | 10 | 10 | 10 | 20 | 20 |
| | M5 | 10 | 20 | 20 | 30 | 30 |

TABLE 3

| | | Irradiance (mW/cm$^2$) 0.1 Integrated Irradiation Dose (mJ/cm$^2$) | | | | | |
|---|---|---|---|---|---|---|---|
| | | 0.5 | 1.0 | 2.0 | 10.0 | 30.0 | 50.0 |
| Evaluator | M1 | 10 | 20 | 20 | 20 | 30 | 30 |
| | M2 | 10 | 20 | 30 | 30 | 30 | 40 |
| | M3 | 10 | 10 | 20 | 20 | 20 | 20 |
| | M4 | 10 | 10 | 20 | 20 | 20 | 20 |
| | M5 | 10 | 10 | 20 | 20 | 30 | 40 |

TABLE 4

| | | Irradiance (mW/cm$^2$) 1 Integrated Irradiation Dose (mJ/cm$^2$) | | | | | |
|---|---|---|---|---|---|---|---|
| | | 0.5 | 1.0 | 2.0 | 10.0 | 30.0 | 50.0 |
| Evaluator | M1 | 20 | 20 | 20 | 40 | 40 | 40 |
| | M2 | 20 | 20 | 30 | 30 | 40 | 40 |
| | M3 | 10 | 10 | 20 | 20 | 30 | 40 |
| | M4 | 20 | 20 | 20 | 40 | 40 | 40 |
| | M5 | 10 | 20 | 20 | 30 | 30 | 40 |

Table 5 shown below represents a correspondence relationship between odor index and actual smell (see Non-Patent Document 3).

TABLE 5

| Contents | Odor Index |
| --- | --- |
| Clean Air in Suburban Area | 0 |
| Air in Industrial Area | 5 |
| Flowers of Japanese Plum | 10 |
| Roadside Air | 15 |
| Cosmetic Counters at Department Store | |
| Playing with Fireworks | 20 |
| Bathroom Deodorant | |
| Daphne | |
| Incense Stick | 25 |
| Soy Sauce | |
| Gasoline Fueling | 30 |
| Tobacco | |
| Coffee | 35 |
| Smell of Frying Garlic | 45 |

As can be seen from Table 1, in the case of the irradiance X was 0.003 mW/cm$^2$, three out of the five evaluators judged that the odor index N had reached 20 or more when the integrated irradiation dose Y reached 30.0 mJ/cm$^2$. An odor index N of 20 is generally regarded as corresponding to the strength of the smell of Daphne or a bathroom deodorant, and is therefore regarded as being at a level that can easily be detected. Further, the regulatory standards at site boundary in the regulatory standards based on the Offensive Odor Control Law specify that the odor index should be set to 10 to 21 corresponding to an odor intensity of 2.5 to 3.5 in the six-step odor intensity labeling method. That is, the odor index N of 20 is close to the upper limit specified in the regulatory standards, and is a level at which the generation of a strange odor can be easily detected.

Similarly, the following results were confirmed from Tables 2 to 4.

As can be seen from Table 2, in the case of the irradiance X was 0.01 mW/cm$^2$, four out of the five evaluators judged that the odor index N had reached 20 or more when the integrated irradiation dose Y reached 10.0 mJ/cm$^2$.

As can be seen from Table 3, in the case of the irradiance X was 0.1 mW/cm$^2$, five out of the five evaluators judged that the odor index N had reached 20 or more when the integrated irradiation dose Y reached 2.0 mJ/cm$^2$.

As can be seen from Table 4, in the case of the irradiance X was 1 mW/cm$^2$, three out of the five evaluators judged that the odor index N reached 20 when the integrated irradiation dose Y reached 0.5 mJ/cm$^2$.

Figure 8:
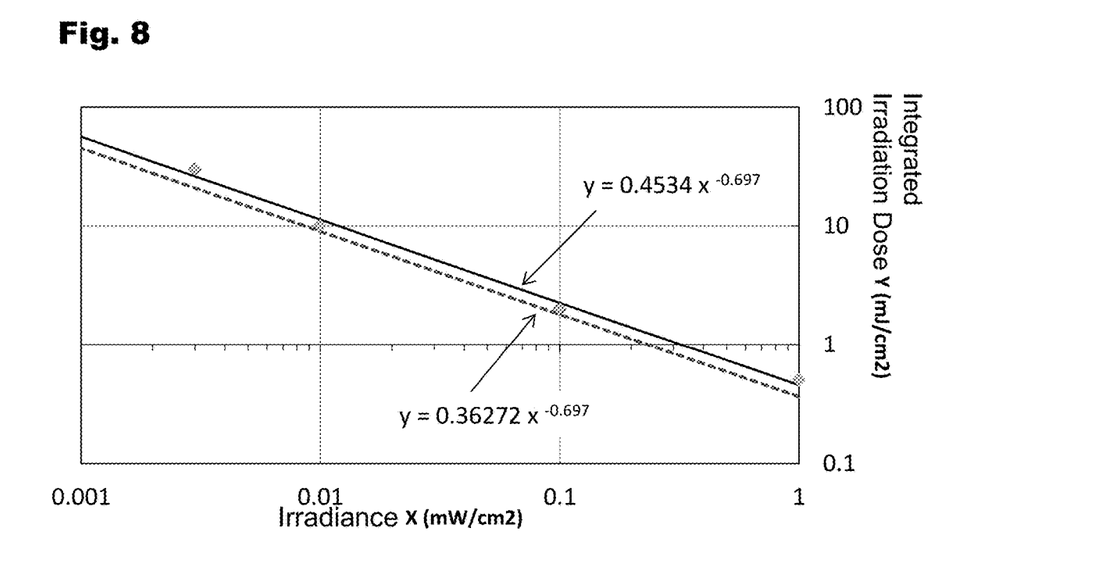
FIG. 8 is a graph obtained by plotting a relationship between the integrated irradiation dose Y and the irradiance X determined by more than half of evaluators as a relationship that allows an odor index N to reach 20 or more.

The above results reveal that the value of the integrated irradiation dose Y at which a strange odor starts to be generated differs according to the value of the irradiance X. FIG. 8 is a graph obtained, on the basis of the results shown in Tables 1 to 4, by plotting a relationship between the integrated irradiation dose Y and the irradiance X determined by more than half of the evaluators (here, three or more evaluators) as a relationship that allows the odor index N to reach 20 or more. In FIG. 8, the horizontal axis represents the irradiance X [mW/cm$^2$], and the vertical axis represents the integrated irradiation dose Y [mJ/cm$^2$]. Further, in FIG. 8, an approximate curve substantially passing through the four points, $Y=0.4534X^{-0.697}$, and a curve obtained in consideration of a safety factor of 0.8, $Y=0.36272X^{-0.697}$ are shown together.

This result reveals that generation of a strange odor can be suppressed by irradiating the ultraviolet light L1 so that a relationship between the irradiance (X) [mW/cm$^2$] (X>0) on the surface (irradiated surface) of the processing target 2 and the integrated irradiation dose (Y) [mJ/cm$^2$] satisfy $Y<0.4534X^{-0.697}$. As described above, since the room 1 is ventilated at least once every two hours, it is presumed that air in the room 1 containing a substance causing a strange odor is exhausted through the door 8 and the air vent 9, so that the concentration of the substance decreases. Therefore, it can be seen that generation of the strange odor can be suppressed by irradiating the ultraviolet light L1 so that the integrated irradiation dose within two hours (Y) satisfies $Y<0.4534X^{-0.697}$. Note that the effect of suppressing the generation of the strange odor can be enhanced by irradiating the ultraviolet light L1 so that $Y<0.36272X^{-0.697}$ is satisfied, which takes into account a safety factor of 0.8.

Further, as can be seen from Table 1, in the case of the irradiance X was 0.003 mW/cm$^2$, three out of the five evaluators judged that the odor index N reached 30 or more when the integrated irradiation dose Y reached 100.0 mJ/cm$^2$. An odor index N of 30 is generally regarded as corresponding to the strength of a smell such as the smell of tobacco in a smoking area, the smell of gasoline at a gas station, or the smell of curry roux present in close vicinity, and is therefore at a very strong level.

Similarly, the following results were confirmed from Tables 2 to 4.

As can be seen from Table 2, in the case of the irradiance X was 0.01 mW/cm$^2$, four out of the five evaluators judged that the odor index N reached 30 or more when the integrated irradiation dose Y reached 50.0 mJ/cm$^2$.

As can be seen from Table 3, in the case of the irradiance X was 0.1 mW/cm$^2$, three out of the five evaluators judged that the odor index N reached 30 or more when the integrated irradiation dose Y reached 30.0 mJ/cm$^2$.

As can be seen from Table 4, in the case of the irradiance X was 1 mW/cm$^2$, four out of the five evaluators judged that the odor index N reached 30 or more when the integrated irradiation dose Y reached 10.0 mJ/cm$^2$.

Figure 9:
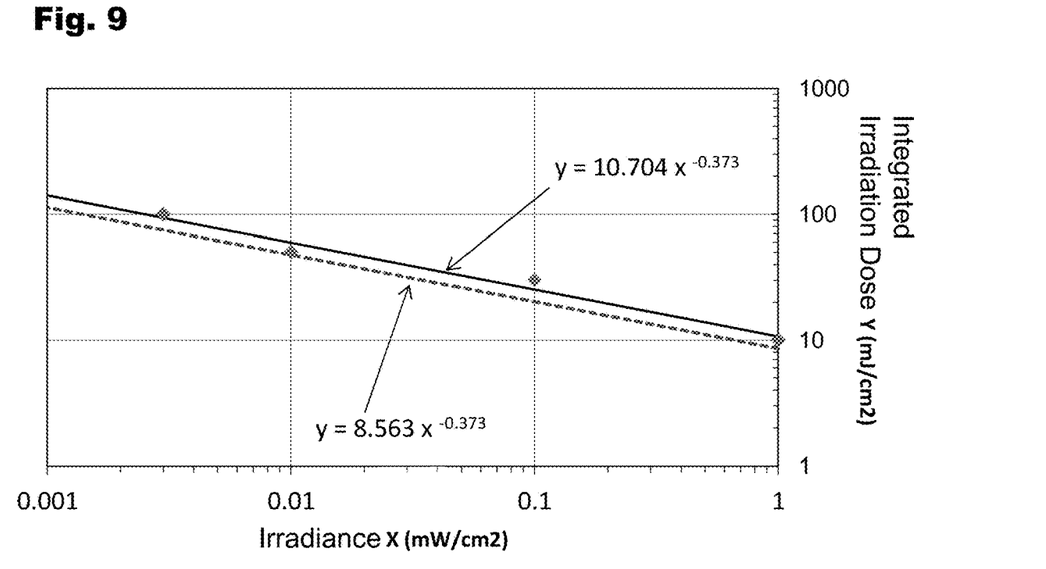
FIG. 9 is a graph obtained by plotting a relationship between the integrated irradiation dose Y and the irradiance X determined by more than half of evaluators as a relationship that allows an odor index N to reach 30 or more.

The above results reveal that the value of the integrated irradiation dose Y at which a very strong odor starts to be generated differs according to the value of the irradiance X. FIG. 9 is a graph obtained, on the basis of the results shown in Tables 1 to 4, by plotting a relationship between the integrated irradiation dose Y and the irradiance X determined by more than half of the evaluators (here, three or more evaluators) as a relationship that allows the odor index N to reach 30 or more. In FIG. 9, the horizontal axis represents the irradiance X [mW/cm$^2$], and the vertical axis represents the integrated irradiation dose Y [mJ/cm$^2$]. Further, in FIG. 9, an approximate curve substantially passing through the four points, $Y=10.704X^{-0.373}$, and a curve obtained in consideration of a safety factor of 0.8, $Y=8.563X^{-0.373}$ are shown together.

This result reveals that generation of a strong strange odor can be suppressed by irradiating the ultraviolet light L1 so that a relationship between the irradiance (X) [mW/cm$^2$] (X>0) on the surface (irradiated surface) of the processing target 2 and the integrated irradiation dose (Y) [mJ/cm$^2$] satisfy $Y<10.704X^{-0.373}$. As described above, since the room 1 is ventilated at least once every two hours, it is presumed that air in the room 1 containing a substance causing a strange odor is exhausted through the air vent 9, the door 8, and gaps, so that the concentration of the substance decreases. Therefore, it can be seen that generation of the strong odor can be suppressed by irradiating the ultraviolet light L1 so that the integrated irradiation dose within two hours (Y) satisfies $Y<10.704X^{-0.373}$. Note that the effect of suppressing the generation of the strong strange odor can be enhanced by irradiating the ultraviolet light L1 so that $Y<8.563X^{-0.373}$ is satisfied, which takes into account a safety factor of 0.8.

In other words, it can be seen that when a relationship between the irradiance (X) [mW/cm$^2$] (X>0) and the integrated irradiation dose (Y) [mJ/cm$^2$] satisfies $0.4534X^{-0.697} < Y < 10.704X^{-0.373}$, some persons sense a smell generated in the room 1, but the strength of the smell can be kept at a low level.

The reason why the lower limit of the integrated irradiation dose Y at which the generation of a strange odor is confirmed varies according to the irradiance X is not clear at present, but the present inventor surmises the following.

An irradiance dependence was confirmed for the sterilization effect of ultraviolet light at 200 nm to 235 nm. That is, it was found that the higher the irradiance, the higher sterilizing capability, even at the same integrated irradiation dose. Therefore, it can be inferred that there is also an irradiance dependency in the decomposition of squalene, in which the reaction proceeds more easily at higher irradiance even the same integrated irradiation dose.

[Examination 2]

For example, an irradiance X of 0.003 mW/cm$^2$ shown in Table 1 is very weak. An experiment was carried out to verify that the inactivation of germs 3 attached to a processing target 2 can be achieved even at such a weak irradiance. Hereinbelow, a test method will be described.

First, 1 mL of *Staphylococcus aureus* having a concentration of about 10$^6$ CFU (Colony Forming Unit)/mL was placed in a Φ35-mm petri dish, and was irradiated with ultraviolet light L1 at a predetermined irradiation dose from above the petri dish. Then, the liquid in the petri dish after irradiation with the ultraviolet light L1 was diluted by a predetermined factor with normal saline, and 0.1 mL of the diluted liquid was inoculated onto a standard agar medium. Then, the inoculated standard agar medium was incubated in a culture environment at a temperature of 37° C. and a humidity of 70% for 24 hours, and the number of colonies was counted.

As a result, it was confirmed that *Staphylococcus aureus* could be inactivated up to 99.7% by irradiation with ultraviolet light for 83 minutes (integrated irradiation dose: about 15 mJ/cm$^2$), even at a very weak irradiance of X=0.003 mW/cm$^2$.

Further, it was found out that the effect of inactivating bacteria can be achieved even when irradiating the ultraviolet light L1 at a very low irradiance X of less than 1 μW/cm$^2$, such as X=0.0002 mW/cm$^2$, X=0.0005 mW/cm$^2$, or X=0.00075 mW/cm$^2$. More specifically, it was confirmed that *Staphylococcus aureus* could be inactivated up to 60% by irradiation with ultraviolet light for 13 hours (integrated irradiation dose: about 10 mJ/cm$^2$), even at a very weak irradiance of X=0.0002 mW/cm$^2$.

Note that when another verification test using Feline coronavirus was carried out in the same manner, an inactivation rate of −2.5 Log was achieved by irradiation with ultraviolet light at an irradiance X of 0.1 mW/cm$^2$ and an integrated irradiation dose Y of 1.5 mJ/cm$^2$. On the other hand, in the case of *Staphylococcus aureus*, irradiation with ultraviolet light at an irradiance X of 0.1 mW/cm$^2$ and an integrated irradiation dose Y of 5 mJ/cm$^2$ is required to achieve the same inactivation rate of −2.5 Log. From the result, it was confirmed that the same number of copies of the virus could be inactivated even when the integrated irradiation dose of the ultraviolet light L1 was about ⅓ of that for the germ.

That is, it can be seen that the inactivating apparatus 5 according to the present invention can inactivate the germs 3 attached to the processing target 2 while suppressing the generation of a strong strange odor by allowing the controller 12 to control the lighting of the light source 11 so that a relationship between the irradiance (X) and the integrated irradiation dose within two hours (Y) satisfies $Y < 10.704X^{-0.373}$, preferably $Y < 8.563X^{-0.373}$. Furthermore, it can be seen that the germs 3 attached to the processing target 2 can be inactivated while significantly suppressing the generation of a strange odor by allowing the controller 12 to control the lighting of the light source 11 so that a relationship between the irradiance (X) and the integrated irradiation dose within two hours (Y) satisfies $Y < 0.4534X^{-0.697}$, preferably $Y < 0.36272X^{-0.697}$.

Figure 10:
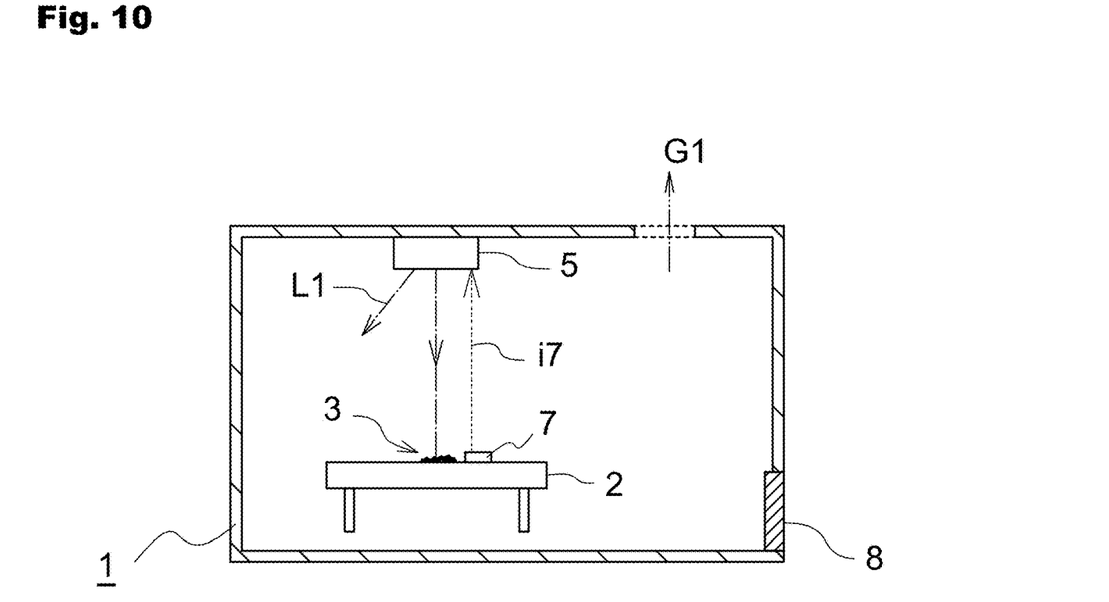
FIG. 10 is another diagram schematically showing a state in which the method for inactivating bacteria or viruses according to the present invention is carried out.
Figure 11:
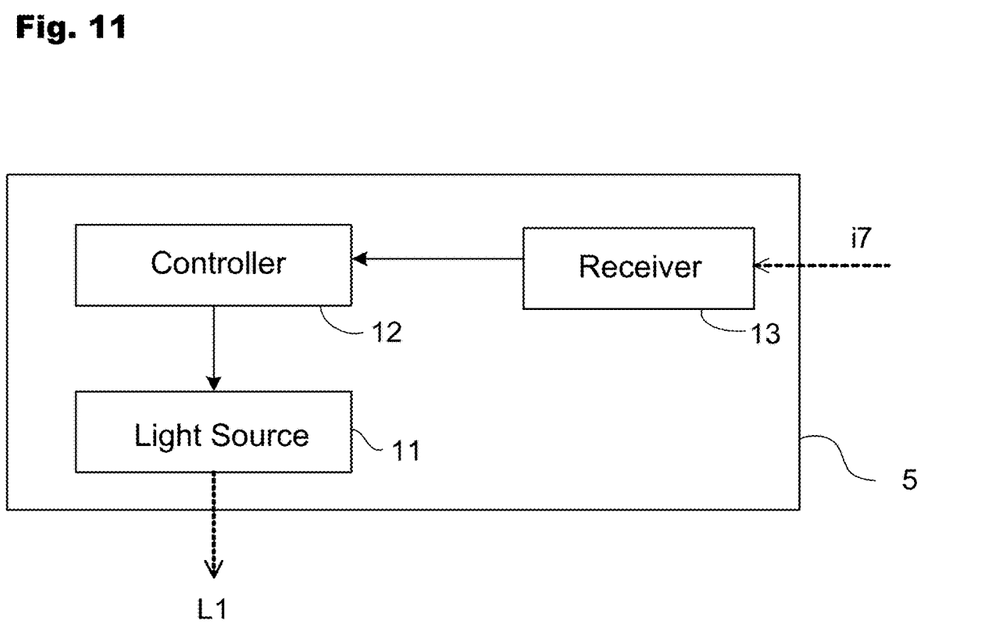
FIG. 11 is another block diagram schematically showing the structure of the inactivating apparatus.

Note that in the present invention, a method for allowing the controller 12 to detect the irradiance X on the surface of the processing target 2 is not particularly limited. For example, as shown in FIG. 10, an irradiance meter 7 may be installed to detect the irradiance X on the surface of the processing target 2. In this case, as shown in FIG. 11, the inactivating apparatus 5 may include a receiver 13 that receives irradiance information i7 transmitted from the irradiance meter 7 so that the controller 12 controls the lighting of the light source 11 to allow a relationship between the irradiance (X) based on the irradiance information i7 and the integrated irradiation dose within two hours (Y) to satisfy $Y < 10.704X^{-0.373}$.

Figure 12:
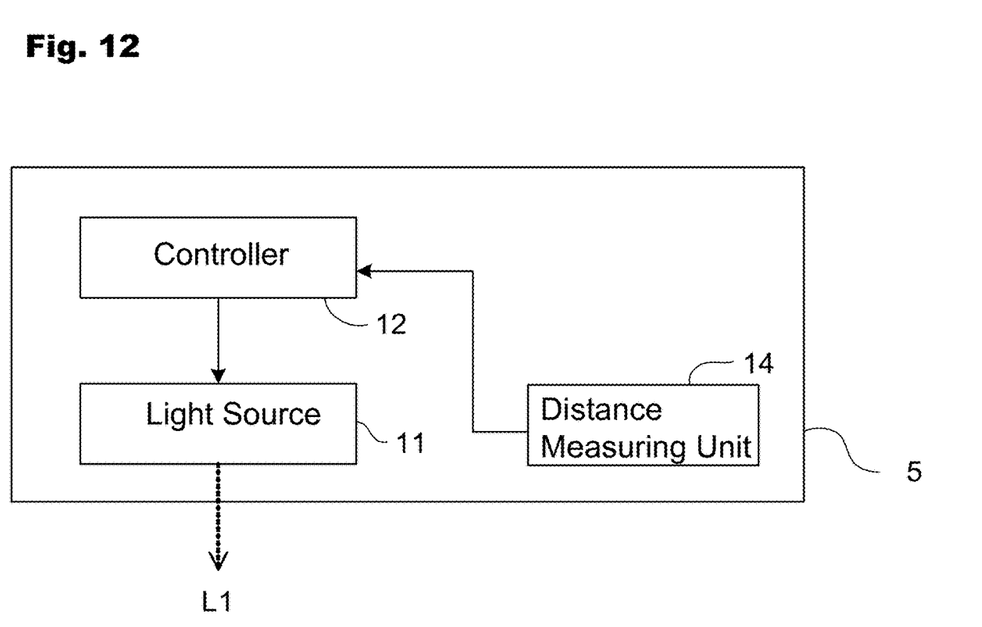
FIG. 12 is another block diagram schematically showing the structure of the inactivating apparatus.

Alternatively, as shown in FIG. 12, the inactivating apparatus 5 may include a distance measuring unit 14, such as a ranging sensor, which measures a distance between the light extraction face of the light source 11 and the surface of the processing target 2. In this case, the controller 12 may calculate the irradiance X on the surface of the processing target 2 from the optical output of the light source 11 and information about the distance measured by the distance measuring unit 14. Further alternatively, even if the inactivating apparatus 5 does not include the distance measuring unit 14, and if the inactivating apparatus 5 is fixed to a ceiling, the controller 12 may calculate the irradiance X on the surface of the processing target 2 from the optical output of the light source 11 and information about a general ceiling height.

As described above, in the inactivating apparatus 5 according to the present embodiment, the controller 12 controls the lighting of the light source 11 so that a relationship between the irradiance (X) and the integrated irradiation dose within two hours (Y) satisfies $Y < 10.704X^{-0.373}$. At this time, as long as the above formula is satisfied, the controller 12 may turn on the light source 11 continuously, may turn on the light source 11 so that the irradiance fluctuates over time or periodically between high and low levels, or may even turn on the light source 11 intermittently. In the case where the light source 11 is turned on so that the irradiance fluctuates over time or periodically, the lighting waveform thereof may be a square wave.

There are individual differences in the ability of detecting an odor. More specifically, even when the ultraviolet light L1 is irradiated under conditions satisfying $Y < 10.704X^{-0.373}$, there is a possibility that some people recognize the presence of an unpleasant odor in the room 1. In addition, since a substance as a source of odor is generated during irradiation with the ultraviolet light L1, intermittent turning on the light source 11 can reduce the amount of the substance as the source of odor generated within the same period of time. Furthermore, when the light source 11 is turned off, air containing odor is diffused by circulation of air in the room 1, which is expected to be effective at making it difficult to detect an odor.

Similarly to the above, the amount of a substance as a source of smell generated during the same period of time can be reduced by turning on the light source 11 so that the irradiance is changed with time or periodically between a high level at which smell is likely to be generated and a low level at which smell is less likely to be generated.

From such a viewpoint, the controller 12 may control the light source 11 so that continuous turning-on of the light source 11 for a predetermined first time and turning-off of the light source 11 for a predetermined second time longer than the first time are repeated. In this case, the duty ratio of the lighting time is preferably 50% or less, more preferably 25% or less, even more preferably 10% or less, particularly preferably 5% or less.

From the same viewpoint, the controller 12 may control the light source 11 so that continuous turning-on of the light source 11 for a predetermined first time and turning-on of the light source 11 for a predetermined second time longer than the first time at a lower emission intensity are repeated.

In either case, the first time and the second time may each be changed.

Other Embodiments

Hereinbelow, other embodiments will be described.

<1> The above embodiment has been described assuming that the processing target 2 is placed in the "room 1". However, the method of the present invention is not necessarily limited to the case where the processing target 2 is placed in "room 1", but can be implemented in the same way in the case where the processing target 2 is placed "in a building" including a corridor, etc. The same method can also be used when the processing target 2 (a seat, an elbow rest, a handle, etc.) is installed in a vehicle such as a train, car, airplane, or ship.

<2> The controller 12 may control the light source 11 so that the light source 11 is automatically turned off or the optical output of the light source 11 is automatically reduced when the integrated irradiation dose within two hours (Y) comes close to $10.704X^{-0.373}$ in relationship with the irradiance (X).

<3> The above embodiment has been described with reference to a case where the light source 11 includes the excimer lamps 23 filled with the light-emitting gas 23G containing KrCl or KrBr. However, as described above, the light source 11 used in the present invention may be the excimer lamp 23 filled with another light-emitting gas 23G, a lamp other than the excimer lamp 23, or a solid-state light source such as an LED or an LD. The structure and luminescence principle of the light source 11 are not particularly limited as long as the light source 11 emits ultraviolet light L1 having an optical output at a specific wavelength in the range of 200 nm to 235 nm.

What is claimed is:

1. A method for inactivating bacteria or viruses, the method comprising a step (a) of continuously or intermittently irradiating with ultraviolet light having an optical output at a specific wavelength in a range of 200 nm to 235 nm to a processing target placed in a building for a period exceeding two hours, and a step (b) of exchanging indoor air one or more times within two hours, wherein the step (a) is a step of irradiating with the ultraviolet light so that an irradiance (X) [mW/cm$^2$] ($0.0002 \leq X \leq 1$) on the surface of the processing target and an integrated irradiation dose over a two-hour time duration (Y) [mJ/cm$^2$] satisfy the following formula (1):

$$0.5 < Y < 10.704 X^{-0.373} \qquad (1).$$

2. The method for inactivating bacteria or viruses according to claim 1, wherein the step (a) is a step of irradiating with the ultraviolet light so that the irradiance (X) [mW/cm$^2$] ($0.0002 \leq X \leq 1$) and the integrated irradiation dose over a two-hour time duration (Y) [mJ/cm$^2$] satisfy the following formula (2):

$$0.5 < Y < 0.4534 X^{-0.697} \qquad (2).$$

3. The method for inactivating bacteria or viruses according to claim 1, wherein the step (a) is a step of irradiating with the ultraviolet light at the irradiance X [mW/cm$^2$] ($X \geq 0.001$).

4. An inactivating system for bacteria or viruses, the system comprising:
   a processing target placed in a room where air is exchanged one or more times within two hours;
   a light source that emits ultraviolet light having an optical output at a specific wavelength in a range of 200 nm to 235 nm; and
   a controller that controls an emission intensity of the light source,
   wherein the controller controls the emission intensity of the light source so that an irradiance (X) [mW/cm$^2$] ($0.0002 \leq X \leq 1$) on the surface of the processing target and an integrated irradiation dose over a two-hour time duration (Y) [mJ/cm$^2$] satisfy the following formula (1):

$$0.5 < Y < 10.704 X^{-0.373} \qquad (1).$$

5. The inactivating system for bacteria or viruses according to claim 4, wherein the controller controls the emission intensity of the light source so that the irradiance (X) [mW/cm$^2$] ($0.0002 \leq X \leq 1$) on the irradiated surface and the integrated irradiation dose over a two-hour time duration (Y) [mJ/cm$^2$] satisfy the following formula (2):

$$0.5 < Y < 0.4534 X^{-0.697} \qquad (2).$$

6. The inactivating system for bacteria or viruses according to claim 4, further comprising an irradiance meter that measures the irradiance (X) on the irradiated surface and sends the measured irradiance (X) to the controller.

7. The inactivating system for bacteria or viruses according to claim 4, wherein the controller controls the light source so that the light source is intermittently turned on while the formula (1) is satisfied.

8. A method for inactivating bacteria or viruses, the method comprising a step (a) of continuously or intermittently irradiating with ultraviolet light having an optical output at a specific wavelength in a range of 200 nm to 235 nm to a processing target placed in a room where indoor air is exchanged at a frequency of 0.5 times/hour or more,
   wherein the step (a) is a step of irradiating with the ultraviolet light so that an irradiance (X) [mW/cm$^2$] ($0.0002 \leq X \leq 1$) on the surface of the processing target and an integrated irradiation dose over a two-hour time duration (Y) [mJ/cm$^2$] satisfy the following formula (1):

$$0.5 < Y < 10.704 X^{-0.373} \qquad (1).$$

9. An inactivating system for bacteria or viruses, the system comprising:
   a processing target placed in a room where indoor air is exchanged at a frequency of 0.5 times/hour or more;
   a light source that emits ultraviolet light having an optical output at a specific wavelength in a range of 200 nm to 235 nm; and a controller that controls an emission intensity of the light source, wherein the controller controls the emission intensity of the light source so that an irradiance (X) [mW/cm$^2$] ($0.0002 \leq X \leq 1$) on the surface of the processing target and an integrated irradiation dose over a two-hour time duration (Y) [mJ/cm$^2$] satisfy the following formula (1):

$$0.5 < Y < 10.704 X^{-0.373} \quad (1).$$

* * * * *